United States Patent
Nowacki et al.

[11] Patent Number: 5,125,397
[45] Date of Patent: Jun. 30, 1992

[54] LITHOTRIPTER CUSHION

[76] Inventors: Christopher Nowacki, 1552 Chickamuga, Long Grove, Ill., 60047; Mark T. Horbal, 2 S. 530 Iroquois Courts West, Warrenville, Ill. 60555

[21] Appl. No.: 571,317

[22] Filed: Aug. 22, 1990

[51] Int. Cl.$^5$ .............................................. A61B 17/22
[52] U.S. Cl. .............................................. 128/24 EL
[58] Field of Search ........................ 128/24 EL, 660.03

[56] References Cited

U.S. PATENT DOCUMENTS

| | | | |
|---|---|---|---|
| 4,539,989 | 9/1985 | Forssmann et al. | 128/24 EL |
| 4,630,607 | 12/1986 | Duinker et al. | 128/24 EL |
| 4,718,421 | 1/1988 | Rohwedder et al. | 128/24 EL |
| 4,805,600 | 2/1989 | Wess et al. | 128/24 EL |
| 4,813,402 | 3/1989 | Reichenberger et al. | 128/24 EL |
| 4,840,166 | 6/1989 | Naser et al. | 128/24 EL |
| 4,858,597 | 8/1989 | Kurtze et al. | 128/24 EL |
| 4,998,528 | 3/1991 | Erhardt | 128/24 EL |

FOREIGN PATENT DOCUMENTS 3544707  6/1987  Fed. Rep. of Germany ... 128/24 EL

Primary Examiner—Lee S. Cohen
Assistant Examiner—Krista M. Pfaffle

[57] ABSTRACT

A cushion is provided in combination with a truncated ellipsoidal lithotripter reflector. The reflector is open at one end, and this end is closed by a diaphragm. The reflector is filled with liquid and a spark gap is provided at the first focus point of the reflector. The second focus point of the ellipsoidal reflector is intended to be positioned coincident with a bodily concretion such as a kidney stone. This cannot always be done with the diaphragm extended to engage the body in which the concretion is located. Thus, the present invention provides in combination with the foregoing a flexible cushion having one end engaging the diaphragm, and the other end thereof being adapted to engage the body having the concretion. A strap or the like encircles the sidewall of the cushion, and the strap is tightened or loosened to increase or decrease the axial length of the cushion, and thereby to provide fluid communication between the spark gap and the concretion.

9 Claims, 2 Drawing Sheets

LITHOTRIPTER CUSHION

BACKGROUND OF THE INVENTION

Lithotripters are now generally well known. It is common to provide a table on which a patient rests, the table having an opening therein for access to the patient's back in the area of the kidneys. The lithotripter reflector is positioned beneath the table, and the diaphragm or membrane over the open upper end thereof extends through the hole and into engagement with the patient's body. There is a maximum expansion possible of the diaphragm or membrane, and this limits the interface with the patient.

A related problem which is solved by the present invention is that the water in the lithotripter reflector must be substantially gas free. Gas or air collects in the water in the lithotripter as a result of sparking across the electrodes. The water must be changed rather frequently to remove the accumulated gas. It is expensive to provide gas free water and to substitute it for the gasey water in the lithotripter.

OBJECTS AND SUMMARY OF THE PRESENT INVENTION

In accordance with the present invention it is an object thereof to provide a water filled cushion forming an interface between the diaphragm or membrane on the open end of the reflector and the patient.

More specifically, it is an object of the present invention to provide a generally cylindrical cushion between the patient and the lithotripter reflector diaphragm or membrane which is axially extendable or reduceable to form an interface between the patient and the reflector, and which may also reduce the amount of water in the reflector that has to be replaced from time to time.

In accordance with the present invention we provide a generally cylindrical shaped cushion made of rubber or plastic material and filled with water. The upper end of the cushion engages the patient, while the lower end engages the diaphragm or membrane at the open upper end of the lithotripter reflector. A strap or belt encircles the cushion. The belt may be tightened or loosened to decrease or increase the circumference of the cushion, and thereby to increase the vertical height thereof, whereby to provide a complete interface between the patient and the reflector diaphragm. The lower end of the cushion may depend well into the reflector, with the diaphragm similarly configured, whereby the reflector contains a much lesser volume of water than usual, thereby greatly reducing the amount of gas free water that must be introduced into the lithotripter reflector from time to time.

THE DRAWINGS

The present invention best will be understood from consideration of the following specification when taken in connection with the accompanying drawings wherein.

DETAILED DISCLOSURE OF THE ILLUSTRATED EMBODIMENTS

Figure 1:
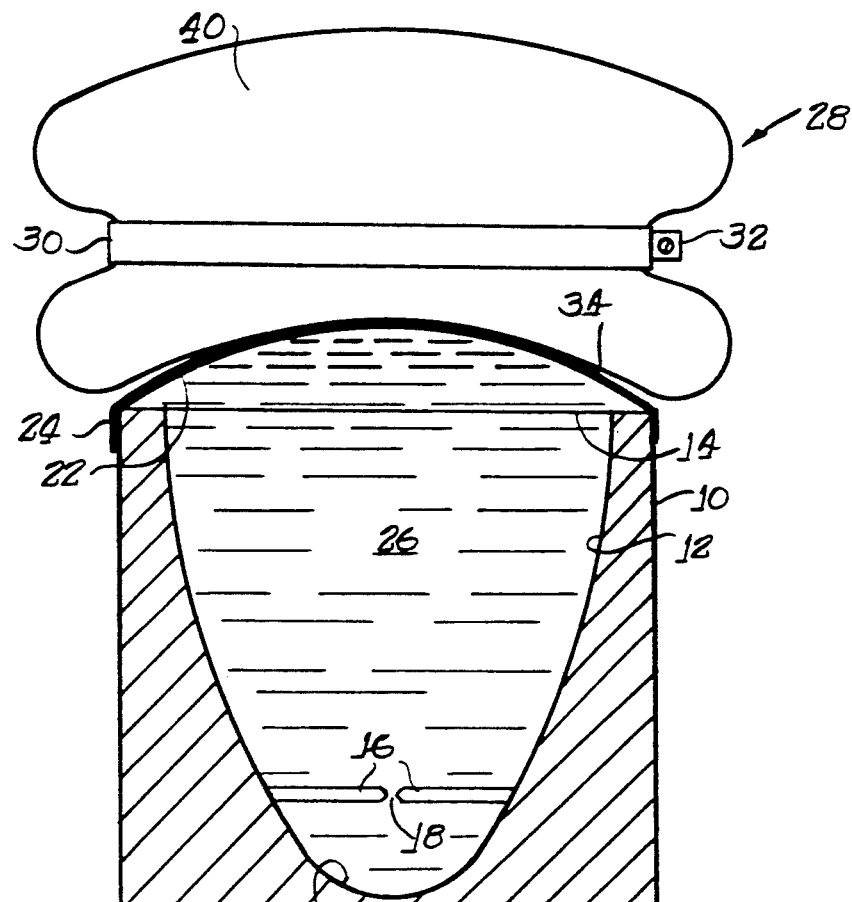
FIG. 1 is an axial sectional view through a lithotripter reflector with the cushion of the present invention shown in outline on the top thereof.

Turning now in greater detail to the figures of the drawing, and first to FIG. 1, there is shown a lithotripter reflector structure 10 having a reflector 12 therein which, as is known, is a truncated portion of an ellipsoid which is open at the upper end as indicated at 14. A pair of electrodes 16 have their tips in spaced relation to provide a gap 18 at the first focus point of the ellipsoid. The second focus point is disposed above the open upper end, and is intended to be coincident with the kidney stone to be disintegrated. It should be noted that reference herein is made to kidney stones, but lithotripters have also found use in destroying gall stones and other bodily concretions. The spark gap 18 is on the rotational axis of the ellipsoid, and is spaced above the apex 20 thereof. A diaphragm or membrane 22 extends across the open upper end 14, and is in the present instance suitable secured by a depending cylindrical portion 24 encircling the open upper end of the reflector structure 10 and suitably secured thereto. The diaphragm 22 is of rubber or plastic construction, and is flexible. The reflector 12 is filled with water as indicated at 26, and the diaphragm may bulge upwardly as indicated in FIG. 1. However, there is a limit to how far this diaphragm may extend upwardly, and this limits proper interfacing of the reflector with the patient.

In accordance with the present invention we provide a cushion 28 which is of generally cylindrical shape, and which is made of a rubber or plastic material. A strap or belt 30 encircles the cylindrical side of the cushion, and is provided with an adjustment 32. This adjustment may be of any suitable type, such as a conventional belt buckle, or a screw threaded arrangement such as commonly used in automobiles for securing hoses to radiators and the like.

As is shown in FIG. 1 the bottom 34 of the cushion 28 assumes a somewhat concave shape as caused by impingement of the diaphragm or membrane 22 against it. On the other hand, the upper end 36 may bulge upwardly in convex configuration as shown. The circumference of the midsection of the cushion can be increased by loosening the strap or belt 30, and conversely it can be decreased by tightening the strap or belt. Loosening of the strap allows the vertical height to decrease, while tightening causes the vertical height to increase.

Figure 2:
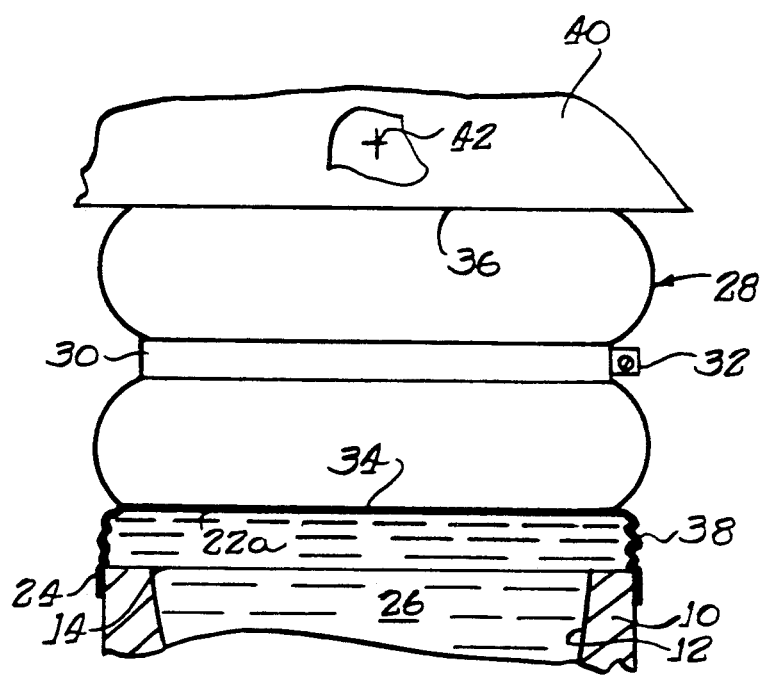
FIG. 2 is a fragmentary view similar to a portion of FIG. 1 showing the cushion further extended and in engagement with the diaphragm and the patient.

The showing in FIG. 2 is generally similar to that in FIG. 1 and the same numbers are used for the same parts. The diaphragm is of a somewhat different type, and therefore is designated as 22a. The distinction is that the diaphragm has an extensible side portion 38 which is pleated somewhat like a bellows. Accordingly, the upper surface of the diaphragm can rise or lower without relying so much on distension of the diaphragm as in FIG. 1, the upper surface of the diaphragm therefore tending to remain generally flat. The underside or bottom 34 of the cushion therefore also is substantially flat, conforming closely to the configuration of the upper portion of the diaphragm. The upper end or surface 36 of the cushion also is shown as somewhat flat, but this shape is determined by engagement with the body of a patient 40 with the positioning being such that the second focus point of the ellipsoidal reflector 12 lies on a kidney stone as indicated at 42 in FIG. 2. It will be understood that generically the "kidney stone" can be any sort of a bodily concretion. As is known, in the use of lithotripters, a spark jumps the gap 18 between the electrodes 16. This creates a shockwave which is reflected from the walls of the reflector 12 and is focused thereby with the shockwave passing through the water 26 in the reflector. In the present invention the shockwave also passes through the water in the cushion 28. The shockwave continues into the body of the patient 40 and is focused on the concretion at 42, whereby the concretion is reduced essentially to dust, and in the case of a kidney stone is passed out along with the urine. The height of the top surface of the diaphragm 22a is to some extent variable in accordance with the pressure of the water 26 in the reflector. The vertical height of the cushion 28 is controllable as previously indicated, by tightening or loosening the strap 30. Accordingly, far less difficulty is encountered in positioning the second focus point of the ellipsoidal reflector precisely on the kidney stone or other concretion 42.

Figure 3:
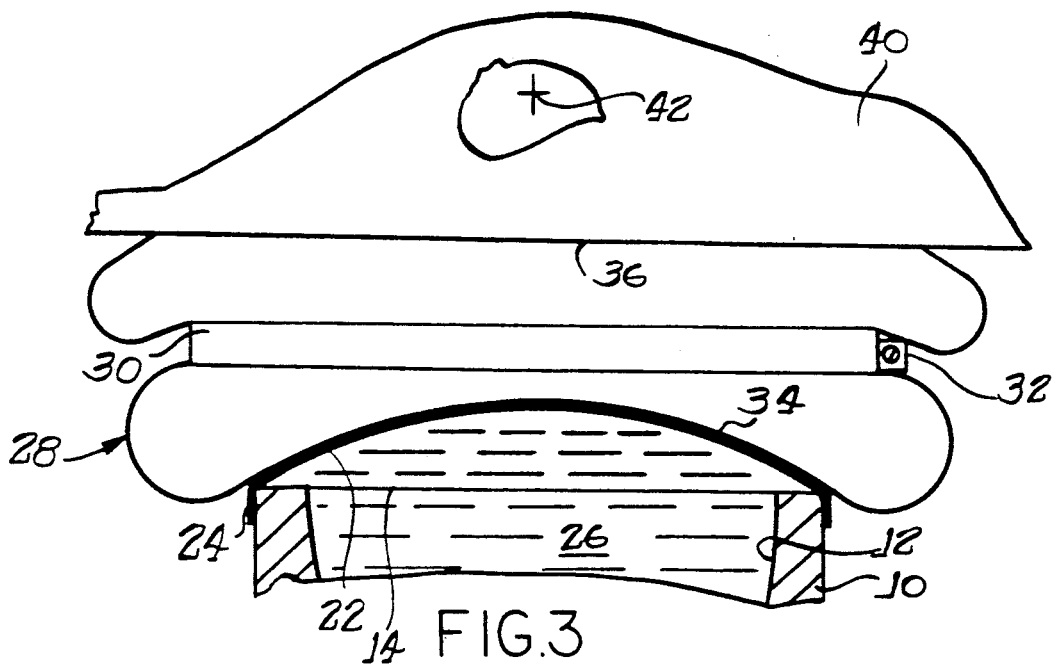
FIG. 3 is a view similar to FIG. 1 showing the diaphragm with the constraining belt loosened to afford a much less vertical height to the cushion.

FIG. 3 is similar to FIG. 2, but with reversion to the original type diaphragm 22. The important distinction is that the belt or strap 30 has been substantially loosened, thereby permitting the outside diameter of the cushion 28 to increase, and the vertical height thereof to decrease. The lower surface or end 34 of the cushion again conforms to the upper surface 22 of the diaphragm, while the upper end or surface 36 of the cushion conforms to the shape of the body of the patient 40. It will be noted that the kidney stone or other concretion 42 is shown as substantially higher in the patient's body in FIG. 3 than in FIG. 2, and it is for this reason that the vertical height of the cushion is decreased. The position of the concretion may vary quite considerably in accordance with the body weight of the patient, or with particular kidney location and the position of a stone within the kidney, or with some other type of concretion, such as a gall stone.

Figure 4:
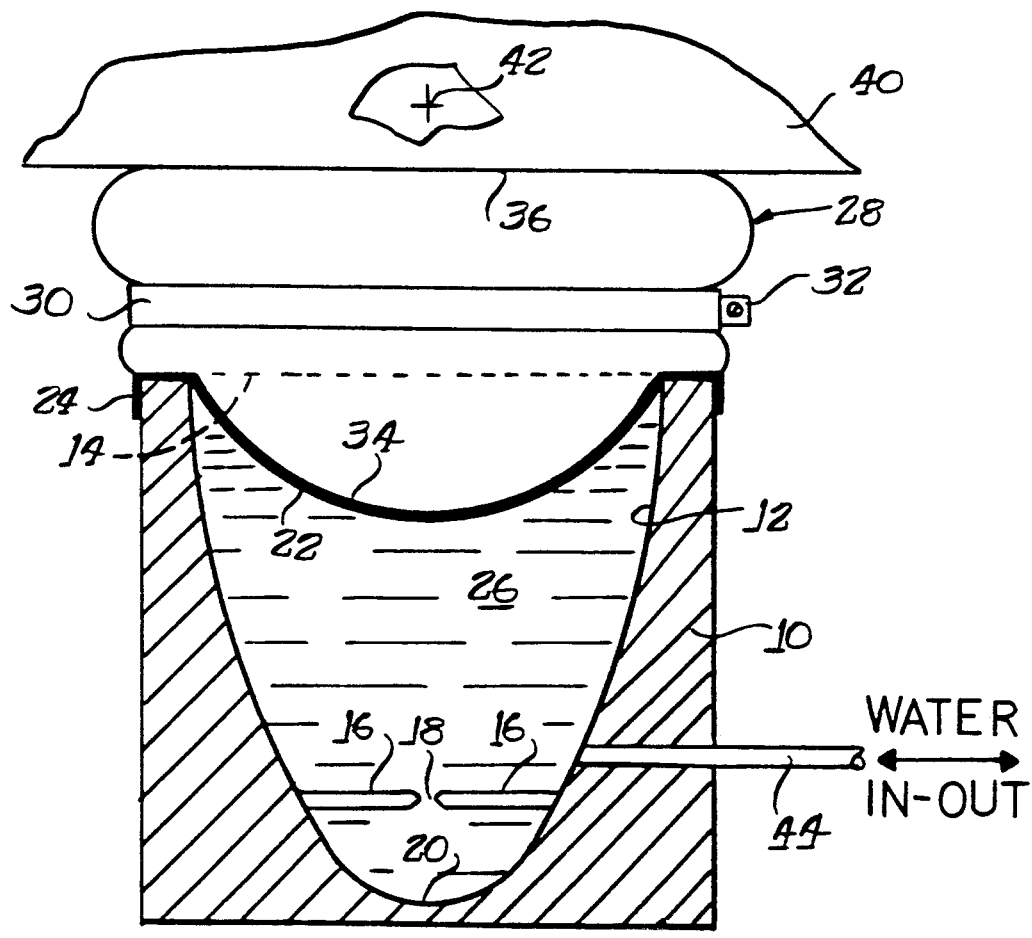
FIG. 4 is a view generally similar to the foregoing figures, but showing the cushion as depending partway into the reflector to minimize the amount of water required in the reflector.

In FIG. 4 the diaphragm 22 is positioned so as to sag well down into the reflector 12. In accordance therewith, the lower end 34 of the cushion also sags down into the reflector in conformity with the shape of the diaphragm 22. This can be controlled, along with the overall height of the upper surface 36 above the upper end 14 of the reflector by tightening or loosening the strap or belt 30. A pipe 44 is shown for passing water into the reflector or out thereof. It will be understood that two pipes could be used, one for water in, and one for water out. The essential distinction to be seen in FIG. 4 is that the water 26 does not have to be supplied in nearly as much quantity as in FIGS. 1-3, because of the sagging of the diaphragm 22 into the cavity. It will be understood that FIG. 4 is illustrative only, and that in actual practice the diaphragm would extend much further down into the reflector, so that the usual volume of 10-12 liters of water could be reduced to as little as 2 liters that would have to be changed from time to time. As is shown, the outside diameter of the cushion is greater than that of the reflector 12, even with the strap constricted to the point where the cushion has its maximum axial length. The diameter of the cushion and of the belt in the belt area with the cushion pinched into a minimum diameter at that point is on the order of 30 centimeters in one example. The cushion can be sealed or refillable, and it can be used either with or without a sonic lens, the later being known in the lithotripter art.

It will now be seen that the cushion of the present invention can be changed quite considerably in its axial length by the simple expedient of tightening or loosening the belt 30, thereby to facilitate positioning of the reflector structure 10 so that the kidney stone or other bodily concretion 42 is readily positioned at the second focus point of the ellipsoidal reflector 12.

The specific examples of the invention as herein shown and described will be understood as being for illustrative purposes only. Various changes in structure will no doubt occur to those skilled in the art, and will be understood as forming a part of the present invention, insofar as they fall within the spirit and scope of the appended claims.

The invention is claimed as follows:

1. In a lithotripter comprising a truncated ellipsoidal reflector having an axis of rotation and an open end, a flexible diaphragm overlying and closing said reflector open end, said reflector being filled with a liquid, said reflector having an apex opposite said pen end, and a first focus point adjacent said apex, means providing a spark gap adjacent said first focus point, said ellipsoidal reflector having a second focus point disposed beyond said open end and adapted to be positioned substantially coincident with a bodily concretion, the improvement comprising a cushion filled with a liquid and having first and second ends and an intermediate side wall, one of said ends engaging diaphragm and the other end being adapted to engage a body having said bodily concretion therein, means encircling said sidewall for tightening and loosening respectively to position said ends relatively farther apart or closer together to aid in positioning said second focus point substantially coincident with said bodily concretion.

2. The combination as set forth in claim 1 wherein said diaphragm extends axially beyond said open end of said reflector, whereby the end of said cushion engaging said diaphragm is spaced at least in part axially beyond said open end of said reflector.

3. The combination as set forth in claim 1 wherein said diaphragm is displaced at least in part within said reflector from said open end thereof, whereby the end of said cushion engaging said diaphragm extends at least in part into said reflector from said open end.

4. The combination as set forth in claim 3 wherein said reflector has an annular surface about the open end perpendicular to the axis of rotation, a part of said diaphragm and a part of said cushion engaging said diaphragm being positioned by said annular surface.

5. The combination as set forth in claim 1 wherein the means encircling the sidewall of the cushion comprises a strap.

6. The combination as set forth in claim 5 wherein said encircling means further includes means for decreasing or increasing the circumference of said strap.

7. The combination as set forth in claim 1 wherein said sidewall is substantially cylindrical.

8. The combination as set forth in claim 1 wherein said ends of said cushion are substantially flat.

9. The combination as set forth in claim 7 wherein said ends of said cushion are substantially flat.

* * * * *